(12) United States Patent
Nakamura et al.

(10) Patent No.: US 7,778,683 B2
(45) Date of Patent: Aug. 17, 2010

(54) BLOOD RHEOLOGY MEASUREMENT DEVICE AND BLOOD RHEOLOGY MEASUREMENT METHOD

(75) Inventors: Takahiko Nakamura, Chiba (JP); Masataka Shinogi, Chiba (JP); Fumio Kimura, Chiba (JP); Mizuaki Suzuki, Chiba (JP)

(73) Assignee: Seiko Instruments Inc. (JP)

( * ) Notice: Subject to any disclaimer, the term of this patent is extended or adjusted under 35 U.S.C. 154(b) by 1144 days.

(21) Appl. No.: 11/346,824

(22) Filed: Feb. 3, 2006

(65) Prior Publication Data
US 2006/0178580 A1 Aug. 10, 2006

(30) Foreign Application Priority Data
Feb. 9, 2005 (JP) .............................. 2005-033413

(51) Int. Cl.
*A61B 5/05* (2006.01)
(52) U.S. Cl. ........................ 600/415; 600/454; 600/456; 600/300
(58) Field of Classification Search ................. 600/415, 600/437, 407, 310, 300; 702/48, 6; 356/364, 356/39
See application file for complete search history.

(56) References Cited

U.S. PATENT DOCUMENTS 6,031,942 A * 2/2000 Nakayama ................... 382/284
2003/0032869 A1 * 2/2003 Muramatsu et al. ......... 600/300

* cited by examiner

*Primary Examiner*—Long V Le
*Assistant Examiner*—Joel F Brutus
(74) *Attorney, Agent, or Firm*—Adams & Wilks (57) ABSTRACT

A blood rheology measurement device and a blood rheology measurement method which detect a fingerprint or a vein to thereby measure a positional relation between an artery in a living body and a sensor on the same conditions for each subject during non-invasive measurement and which correctly evaluate a change of blood rheology with elapse of time. A vein pattern or a fingerprint pattern peculiar to a subject is detected, recognized, and stored, a position of a sensor is adjusted so that the detected vein pattern or fingerprint pattern agrees with the stored vein pattern or fingerprint pattern every measurement, and a blood rheology index value indicating blood fluidity (fluidity/viscosity) is measured.

12 Claims, 11 Drawing Sheets

BLOOD RHEOLOGY MEASUREMENT DEVICE AND BLOOD RHEOLOGY MEASUREMENT METHOD

BACKGROUND OF THE INVENTION

1. Field of the Invention

The present invention relates to a blood rheology measurement device and a blood rheology measurement method which measure blood rheology indicating a fluidity generally referred to as fluidity/viscosity of blood, more particularly to a technology to measure a flow of blood flowing through an artery, ascertain a micro circulating blood flow as a base of activity of human body tissue, and perform evaluation of health, diagnosis of disease, evaluation of effect of medicine and the like.

2. Description of the Related Art

To perform evaluation of human health, diagnosis of disease, evaluation of medicine effect on human body, evaluation of soundness and functionality of food and the like, heretofore blood rheology has been measured to perform the evaluation or the diagnosis from measurement results. As a conventional technology using a blood fluidity measurement device, there is known a method in which blood is sampled from a subject, and the blood rheology is measured from a time for which the blood passes under a constant pressure by use of a micro channel array prepared by a lithographic process (see "Measurement of Fluidity of Whole Blood by use of Capillary Blood Vessel. Model" (Food Research Result Information, No. 11 issued in 1999)).

However, in the blood rheology measurement method using the micro channel array as in the conventional technology, to sample the blood from the subject, an injection needle has to be stuck to an elbow part to sample the blood. Therefore, if an in vitro test is performed to check an influence of a food ingredient on the blood rheology, there is a problem that the blood cannot be sampled from the same person many times a day, and it is difficult to continuously perform the test. If the person tries to sample his own blood to measure the blood rheology at home or the like outside a medical institution by the blood fluidity measurement device as in the conventional example, this is impossible because the device cannot be installed, and an appropriate treatment cannot be performed at home. Therefore, there is a problem that the rheology can be measured in the medical institution only.

On the other hand, it is considered that there is a strong correlation between the blood rheology and a blood flow rate in an artery of a living body. That is, it is supposed that the blood flow rate is low in a case where blood viscosity is high, and high in a case where the viscosity is low. Therefore, the blood flow rate in the living body can be measured to know the blood rheology indirectly (see, e.g., Japanese Patent Application Laid-Open No. 2003-159250).

However, in a case where the measurement is non-invasively performed, it is difficult to grasp a position of the artery in the living body in detail. Therefore, a positional relation between a sensor and the artery might differ every time the relation is measured. There is disadvantageously a possibility that a change of the blood rheology with elapse of time cannot be correctly evaluated during measurement of the change with the elapse of time.

An object of the present invention is to provide a blood rheology measurement device which measures a positional relation between an artery in a living body and a sensor on the same conditions for each subject during non-invasive measurement and which correctly evaluates a change of blood rheology with elapse of time.

SUMMARY OF THE INVENTION

To solve the above-described problems, a blood rheology measurement device of the present invention utilizes a fact that a relative position of a vein or fingerprint with respect to an artery of a living body changes owing to individual growth, but does not rapidly change. Specifically, the device has a function of: detecting, recognizing, and storing a vein pattern peculiar to a subject utilizing a fact that infrared light is absorbed by the vein in the living body; and adjusting a position of a sensor so that the detected vein pattern agrees with the stored vein pattern every measurement, thereby solving the above-described problems. Alternatively, the device has a function of detecting a fingerprint on the surface of the living body, and recognizing a fingerprint pattern to adjust a measurement position, thereby solving the above-described problems.

There can be provided a blood rheology measurement device which transmits and receives an ultrasonic wave from the surface of a living body to an artery in the living body to obtain blood rheology and which further recognizes a pattern of a vein or a fingerprint to measure a positional relation between the artery in the living body and a sensor on the same conditions every subject, so that it is possible to correctly evaluate a change of the blood rheology with elapse of time.

DESCRIPTION OF REFERENCE NUMERALS

1 sensor unit
11 ultrasonic wave sensor A
111 transmitting element A
112 receiving element A
12 ultrasonic wave sensor B
121 transmitting element B
122 receiving element B
13 photo sensor 131 transmitting element
132 receiving element
14 acoustic matching layer
2 circuit unit
21 ultrasonic wave transmitting circuit
22 ultrasonic wave receiving and detecting circuit
23 sensor unit moving circuit
24 light emitting circuit
25 light receiving circuit
3 calculation unit
31 FFT calculation processing section
32 blood rheology index calculation processing section
33 image processing section
34 database collating section
35 information acquiring section
4 output unit
5 living body
51 skin
52 artery
53 living tissue
54 vein
55 vein recorded in database
56 fingerprint
57 fingerprint recorded in database

DETAILED DESCRIPTION OF THE INVENTION

Figure 1:
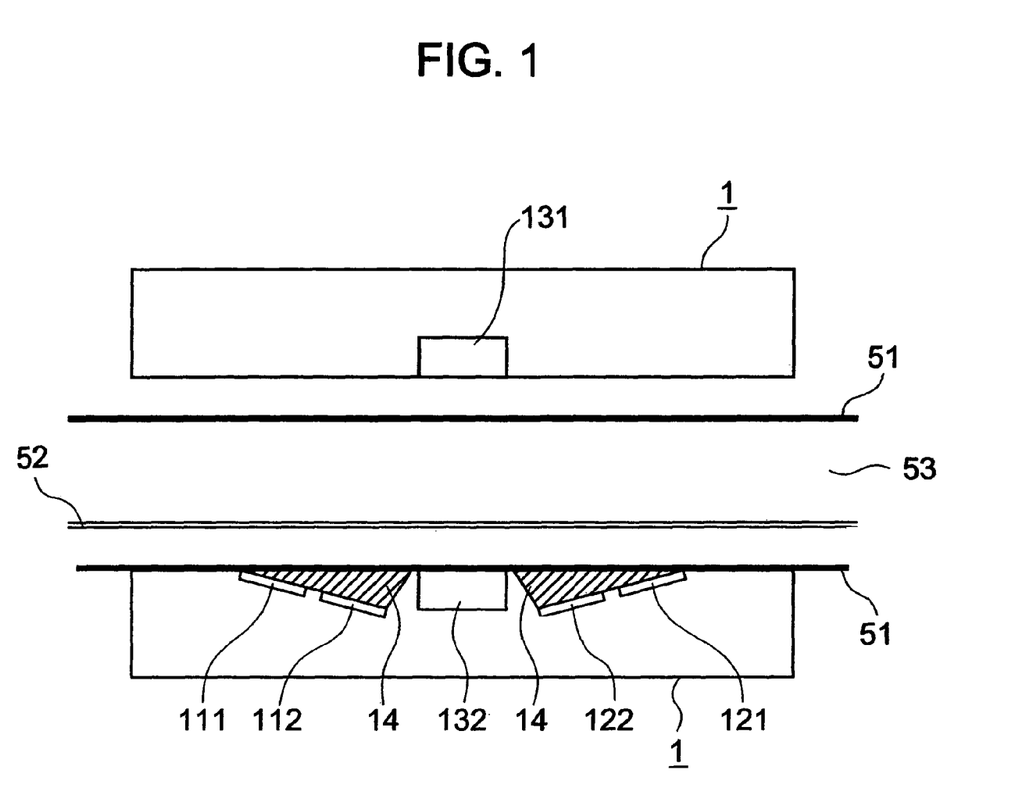
FIG. 1 is a diagram showing one example of a measurement cross-section.
Figure 2:
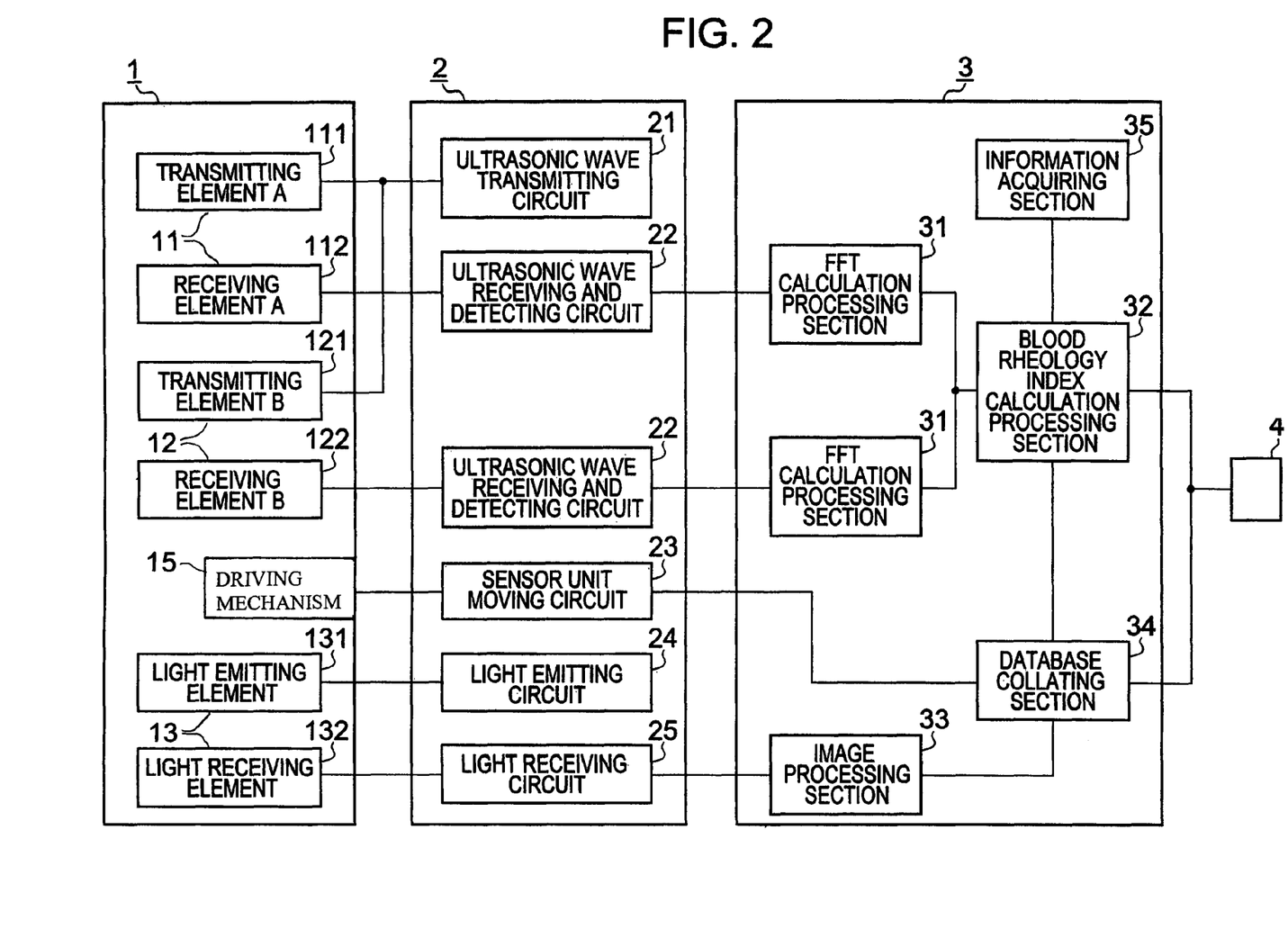
FIG. 2 is a block diagram showing one example of a constitution of a blood rheology measurement device.

FIG. 1 schematically shows a sectional view for measurement in the present invention, and FIG. 2 is a block diagram showing one example of a constitution of a blood rheology measurement device in the present invention.

A sensor unit 1 is constituted of two pairs of ultrasonic wave sensors A 11 and ultrasonic wave sensors B 12 and a photo sensor 13. The ultrasonic wave sensor A 11 is constituted of a transmitting element A 111 and a receiving element A 112, and the ultrasonic wave sensor B 12 is constituted of a transmitting element B 121 and a receiving element B 122. A piezoelectric element such as PZT is suitable for these transmitting and receiving elements. The sensor unit 1 is provided with acoustic matching layers 14 for smoothly transmitting and receiving ultrasonic waves between these transmitting and receiving elements and skin 51. A plurality of acoustic matching layers are disposed, and a surface layer is made of a soft resin closely attachable to the skin 51. Accordingly, it is possible to eliminate an air layer between wrinkles or fingerprints of the skin 51 and the sensor unit 1, so that the ultrasonic waves can be efficiency transmitted and received.

Figure 3:
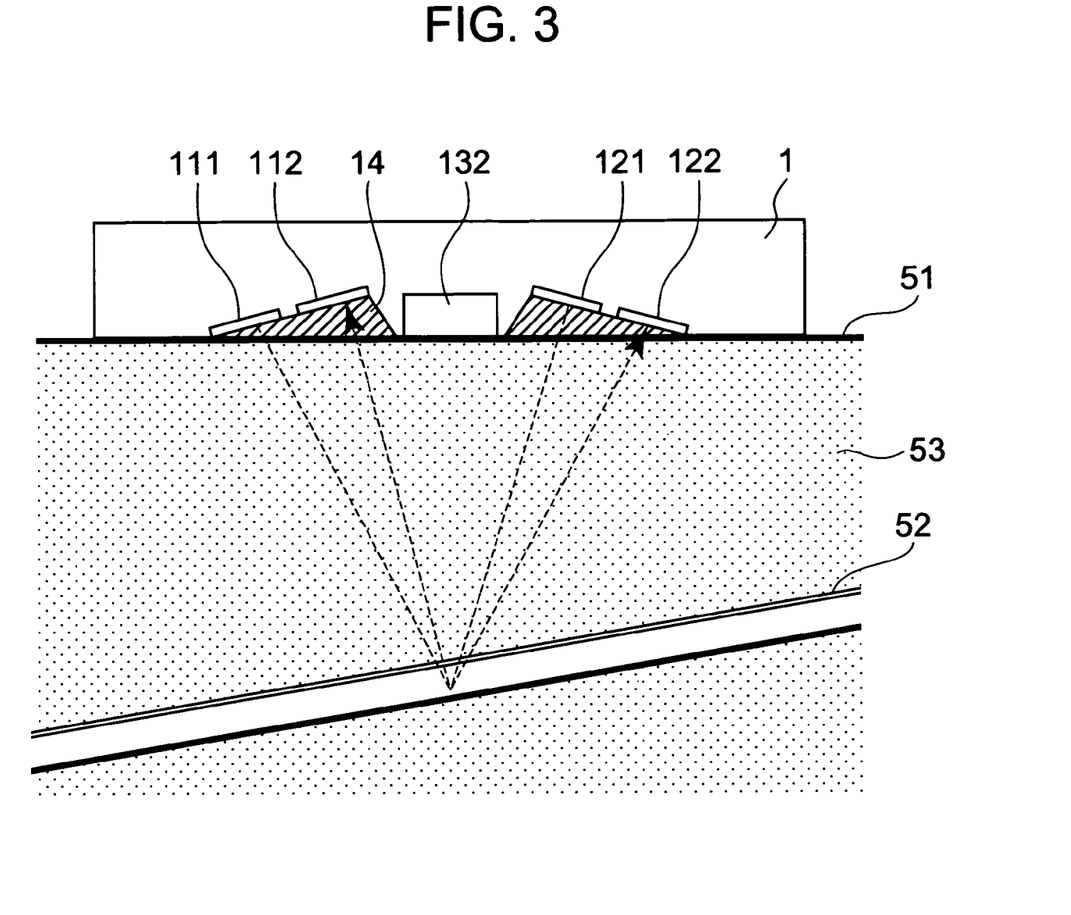
FIG. 3 is a diagram showing one example of the measurement cross-section.

A reason why the sensor unit 1 is provided with two pairs of ultrasonic wave sensors will be described. A blood vessel in a living body does not necessarily run in parallel with the surface of a living body. As shown in FIG. 3, the blood vessel may be oblique with respect to the surface of the living body, that is, the skin 51. An angle formed between the sensor unit 1 and an artery 52 is obtained from the Doppler shift amount obtained from two pairs of ultrasonic wave sensors, so that a blood flow rate can be obtained correctly. The sensor unit 1 is incorporated in a housing of a main body of the device, and the sensor unit 1 is connected to a circuit unit 2 via a flexible wiring substrate or the like (not shown). As shown in FIG. 3, artery positions such as angles and intervals of the ultrasonic wave sensors 11 and 12 are designed so that a portion where the ultrasonic wave transmitted and received by the ultrasonic wave sensor 11 intersects with that transmitted and received by the ultrasonic wave sensor 12 overlaps with the artery 52 to be measured. Accordingly, correct measurement is possible in various measurement portions.

Figure 4:
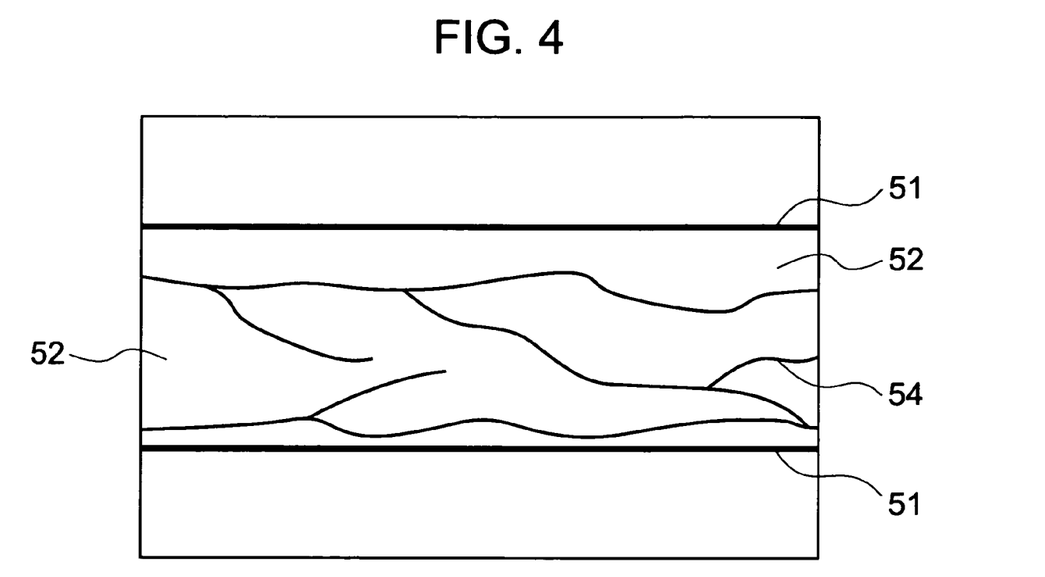
FIG. 4 is a diagram showing a vein pattern.

The photo sensor 13 is constituted of a light emitting element 131 and a light receiving element 132, and light can be transmitted through a living body 5 to obtain a vein pattern as shown in FIG. 4. An LED having a wavelength of 740 nm to 780 nm is used in the light emitting element 131, and a CCD camera is used in the light receiving element 132. FIG. 1 shows a structure for detecting the transmitted light, but a sensor structure for detecting reflected light may be constituted.

The circuit unit 2 is constituted of an ultrasonic wave transmitting circuit 21 which drives the transmitting elements 111 and 121; ultrasonic wave receiving and detecting circuits 22 which receive reception signals from the receiving elements 111 and 122 to detect the Doppler signals; a light emitting circuit 24 which drives the light emitting element 131; a light receiving circuit 25 which receives a signal from the light receiving element 132; and a sensor unit moving circuit 23 for moving the sensor unit 1. Signals of the ultrasonic wave receiving and detecting circuits 22 and the light receiving circuit 25 are sent to a calculation unit 3. The sensor unit moving circuit 23 receives a signal from the calculation unit 3 to move the sensor unit 1 which is attached to, for example, a driving mechanism or moving section 15. Since the driving mechanism 15 for moving the sensor unit 1 can be easily constituted by applying an existing gear mechanism and sliding mechanism, detailed description thereof is omitted. Here, the sensor unit 1 and the driving mechanism 15 constitute detecting means, and FFT calculation processing sections 31, a blood rheology index calculation processing section 32, and an information acquiring section 35 constitute blood rheology measuring means.

The calculation unit 3 is constituted of a fast Fourier transform (FFT) calculation processing sections 31, a blood rheology index calculation processing section 32, an image processing section 33, a database collating section 34, and an information acquiring section 35. The FFT calculation processing sections 31 subject the Doppler signals obtained by the wave receiving and detecting circuits 22 to FFT calculation, and send the results to the blood rheology index calculation processing section 32. The blood rheology index calculation processing section 32 further processes the calculation results of the FFT calculation processing sections 31, and obtains blood rheology from information of a blood pressure, temperature, or a contact pressure between the sensor unit 1 and the living body 5, the information being obtained from the information acquiring section 35. These results are sent to an output unit 4.

The image processing section 33 calculates the signal from the light receiving circuit 25 to thereby prepare a vein pattern, and sends the data to the database collating section 34. The database collating section 34 collates the data obtained by the image processing section 33 every measurement with the data in the database collating section 34 to send a signal to the sensor unit moving circuit 23 if necessary. The database collating section 34 can accumulate results of the blood rheology index calculation processing section 32. The data of the database collating section 34 and the result of the blood rheology index calculation processing section 32 are sent to the output unit 4. Here, the image processing section 33, the database collating section 34, and the sensor unit moving circuit 23 constitute image processing means.

The output unit 4 is a monitor or a speaker, and the data and result from the calculation unit 3 are displayed in a monitor or represented by sound.

In a case where an influence of taken food on the blood rheology is evaluated, the blood rheology is measured at an interval of several minutes. Since artery positions are not known from the surface of the living body in detail, the positional relation between the sensor unit and the artery is not necessarily the same positional relation. However, the vein pattern can be detected to thereby measure the same position. This is because the relative positions of the artery and the vein do not instantly change in a specific subject.

Figure 5:
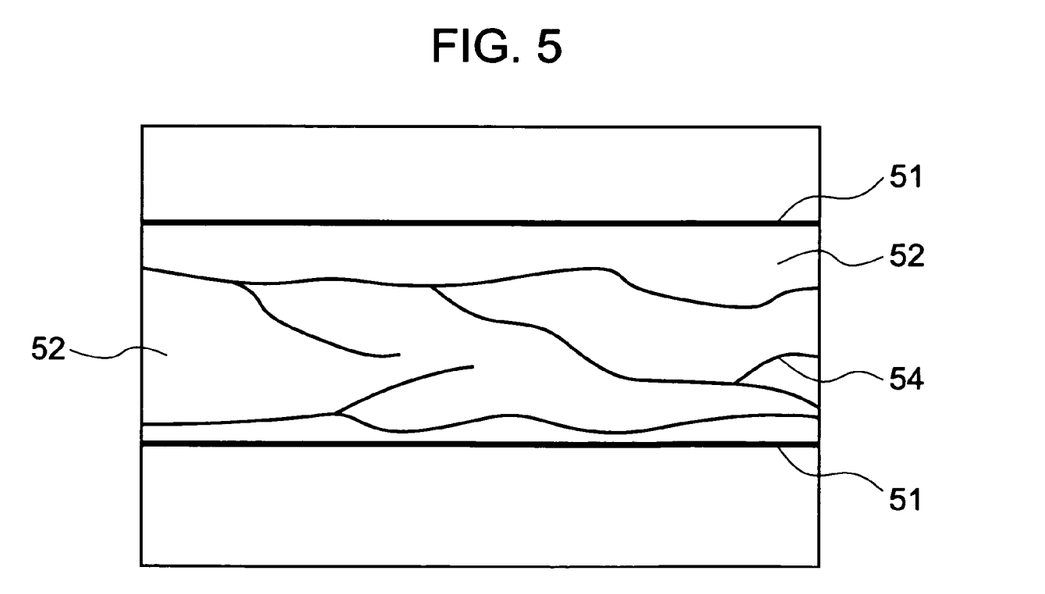
FIG. 5 is a diagram showing the vein pattern.
Figure 6:
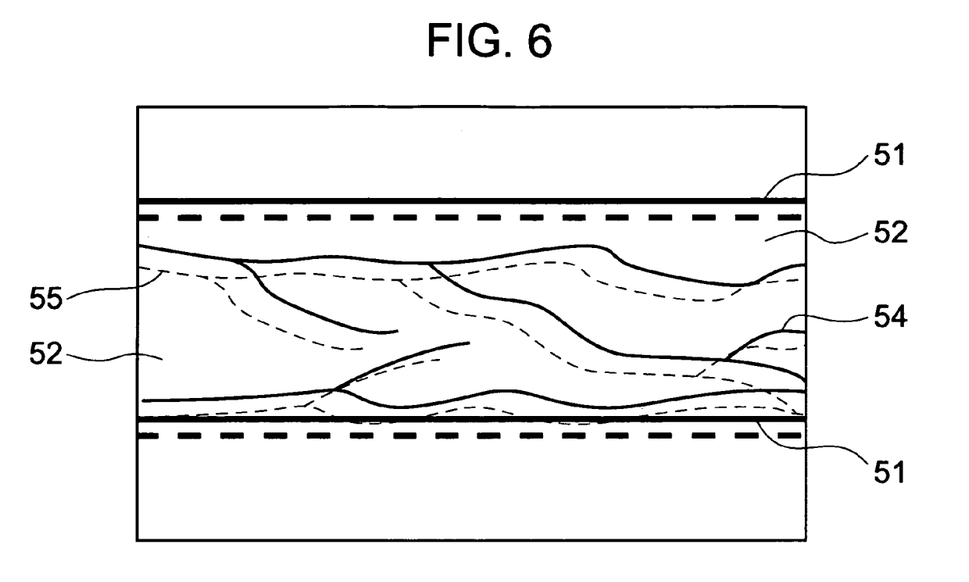
FIG. 6 is a diagram showing a comparative example of the vein pattern.
Figure 7:
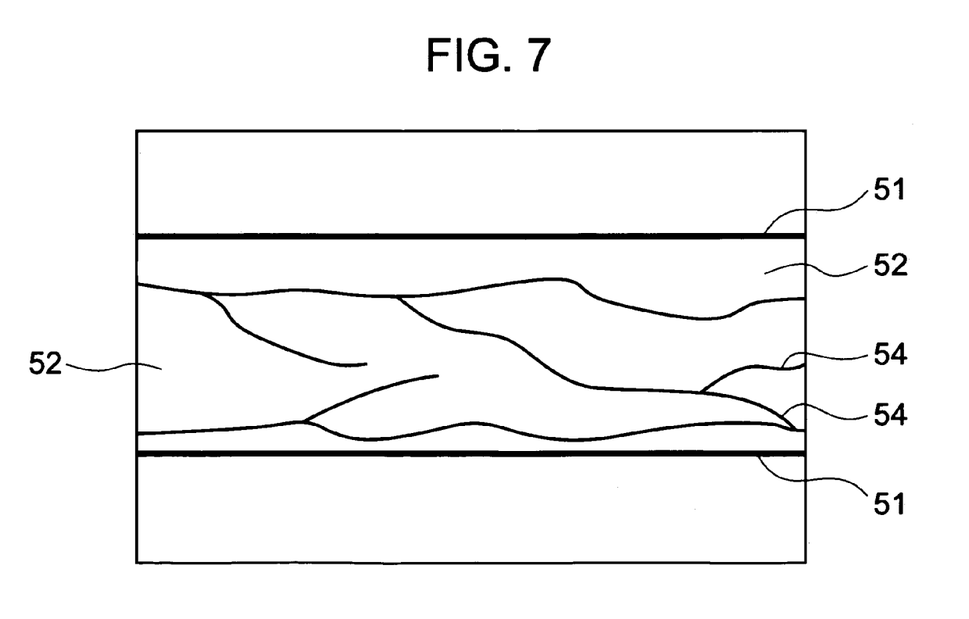
FIG. 7 is a diagram showing an example in which the vein pattern is matched.
Figure 8:
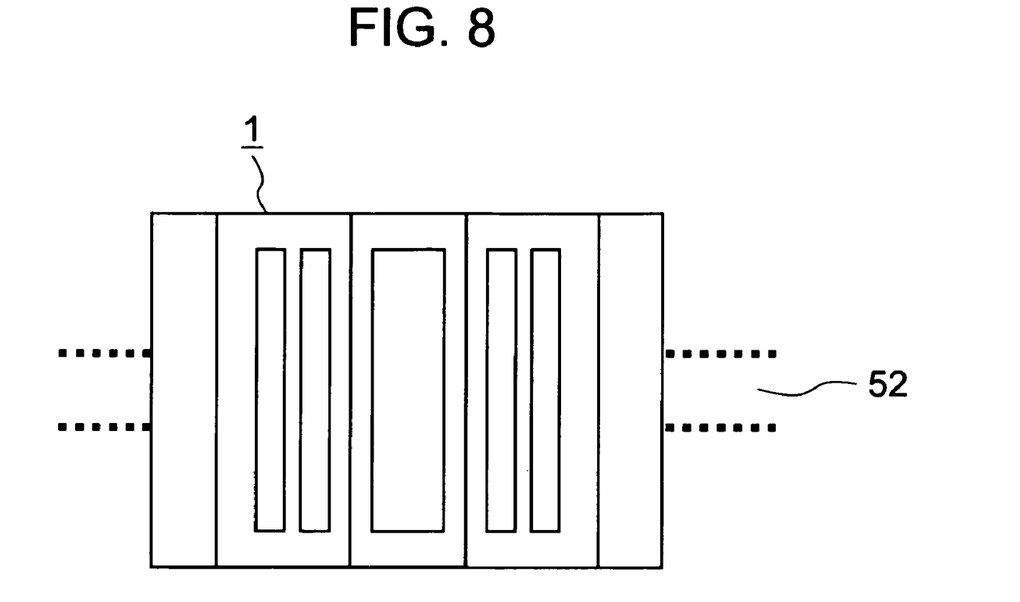
FIG. 8 is a diagram showing a positional relation between a sensor unit and an artery.
Figure 9:
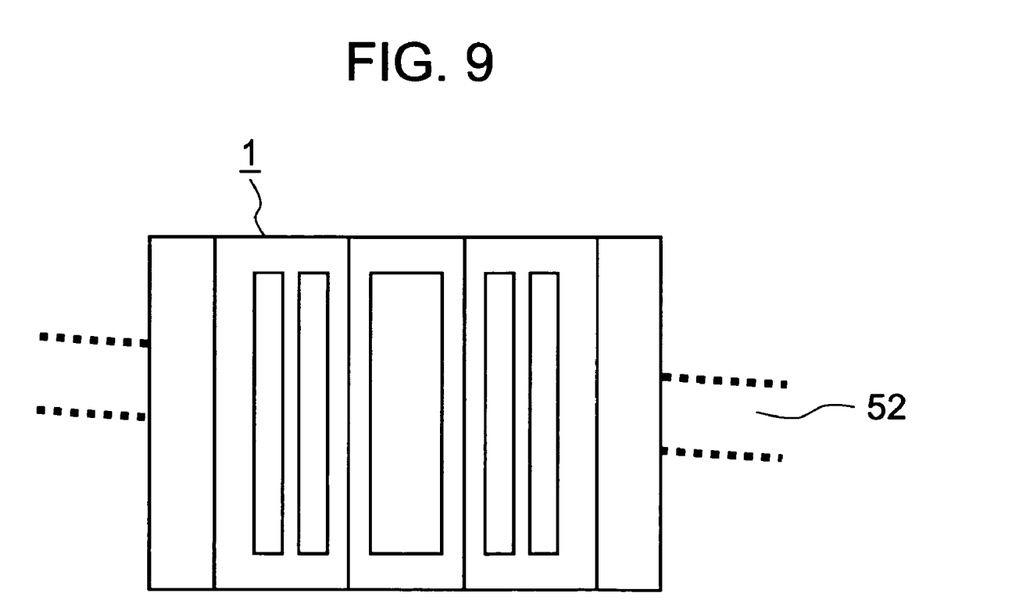
FIG. 9 is a diagram showing a positional relation between the sensor unit and the artery.

FIG. 4 shows one example of the vein pattern. This is obtained by the image processing section 33, when a certain subject performs the measurement. This information is recorded beforehand in the database collating section 34. When this subject performs the measurement anew, a vein pattern shown in FIG. 5 is similarly obtained by the image processing section 33. In this case, the vein pattern recorded beforehand is read and compared with the obtained vein pattern by, for example, superposing one vein pattern over the other as shown in FIG. 6. In a case where there is a discrepancy (i.e., non-registry) between a vein 55 recorded in a database and a measured vein 54, the sensor unit 1 is moved as shown in FIG. 7 to bring the veins 54 and 55 in registry. Since a positional relation between the presently measured vein and the sensor unit agrees with that between the previously measured vein and the sensor unit, a positional relation between the sensor unit and the artery becomes identical. Therefore, the relation between the artery 52 and the sensor unit 1 necessarily becomes consistent depending on the subject, the measurement is necessarily possible with respect to a subject A in a positional relation shown in FIG. 8, and the measurement is necessarily possible with respect to a subject B in a direction shown in FIG. 9.

Moreover, in a case where the influence of the taken food on the blood rheology is evaluated, many subjects perform the measurement. In this case, the subject operates the device before each measurement. Accordingly, the changes of the blood rheology can be evaluated for the individual subjects, but the operation is intricate, and there is a problem that device operation mistakes are made. Since the vein pattern of each subject is peculiar, the subject can be specified by recognizing the vein pattern. The subject's operations in repeated measurements can be remarkably reduced.

Figure 10:
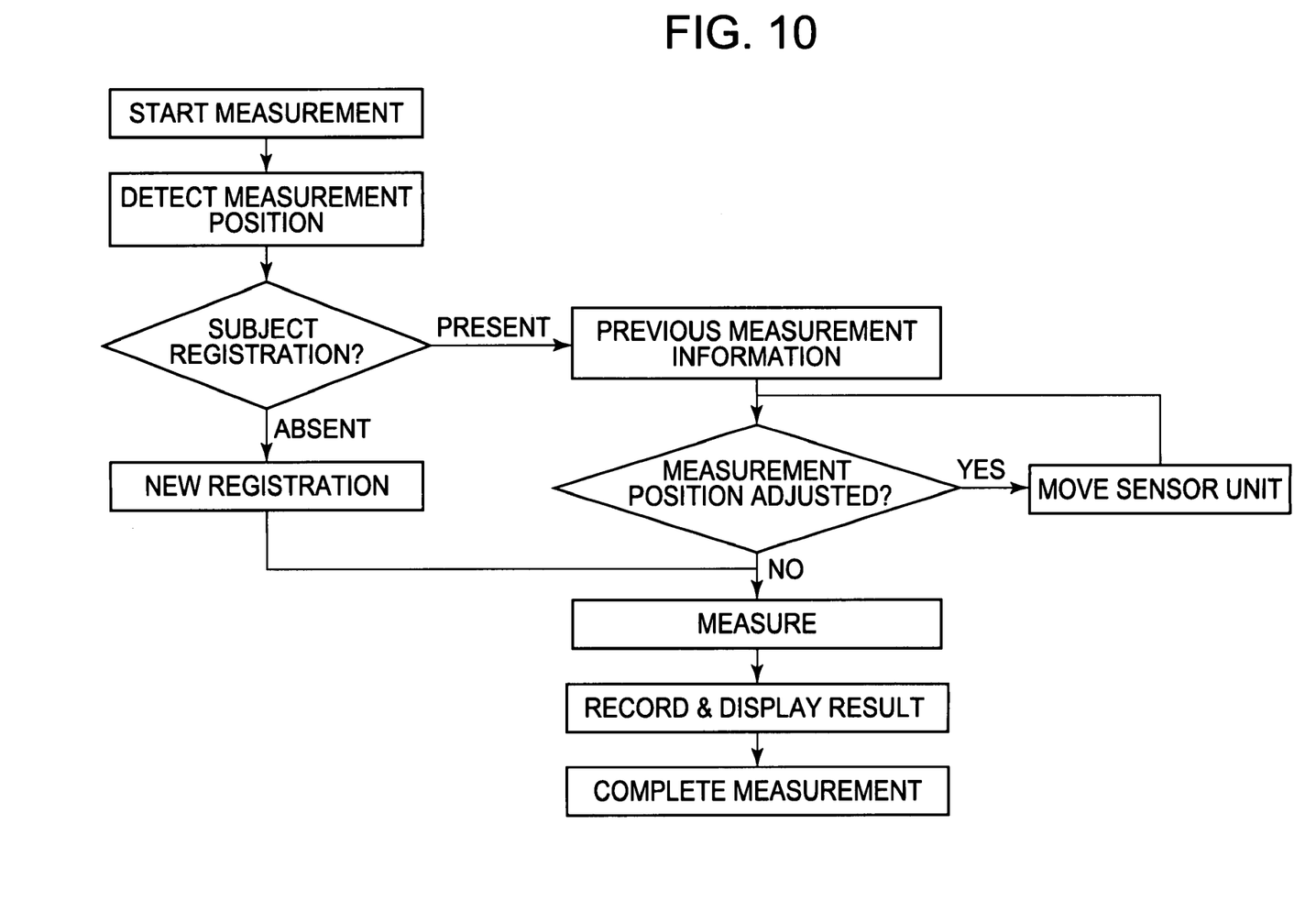
FIG. 10 is a measurement flowchart.

FIG. 10 is a measurement flowchart in the present device which matches subject recognition with the measurement position. When the measurement is started, the measurement position is recognized by the image processing section 33. This data is compared with that stored in the database collating section 34 to judge whether the subject is a subject to be measured first or an already measured subject. When the subject is first to be measured, subject's information such as name, birth date, and gender are recorded to perform blood rheology measurement. Measurement data and position are recorded in the database collating section 34, and the results are exhibited by the output unit 4, thereby completing the measurement.

Figure 11:
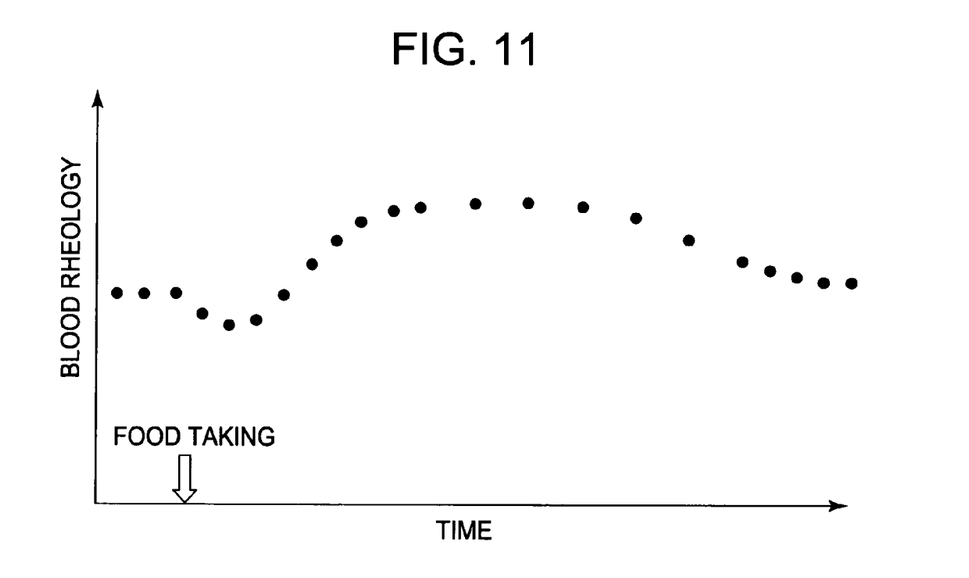
FIG. 11 is a diagram showing a result display example.
Figure 12:
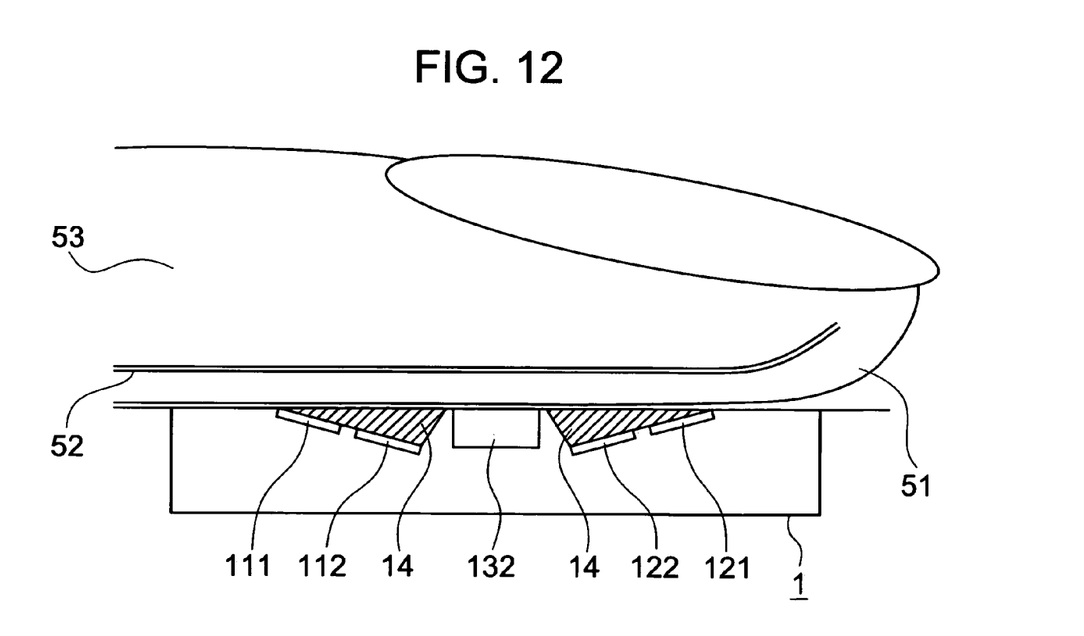
FIG. 12 is a diagram showing one example of the measurement cross-section.

When the subject has been already measured, it is judged whether or not there is a discrepancy in the measurement position. When there is the discrepancy, the sensor unit 1 is moved to judge again whether or not there is a discrepancy in the measurement position. This processing is repeated until the discrepancy is eliminated. When there is not any more discrepancy, the measurement is started. The measurement result is additionally recorded in the database collating section 34. As shown in FIG. 11, the result is exhibited by the output unit 4, thereby completing the measurement. Information such as the measurement result, fluctuations of the blood rheology with time, and name can be browsed only by the subject identified by the vein pattern and an operation manager of a specific device, and personal information can be protected. A password is required for browsing the measurement result, gender and the like of a person other than the subject. Even if a person other than an operation manager obtains the password, the subject's information can be protected because the operation manager can be judged by means of the vein pattern. In a case where there is a wrinkle peculiar to the surface of the living body, that is, fingerprint in a measurement position such as a finger tip portion, the fingerprint can be measured to fix the positional relation between the artery and the sensor. FIG. 12 is a sectional view showing one example of the measurement using the blood rheology measurement device of the present invention.

Figure 13:
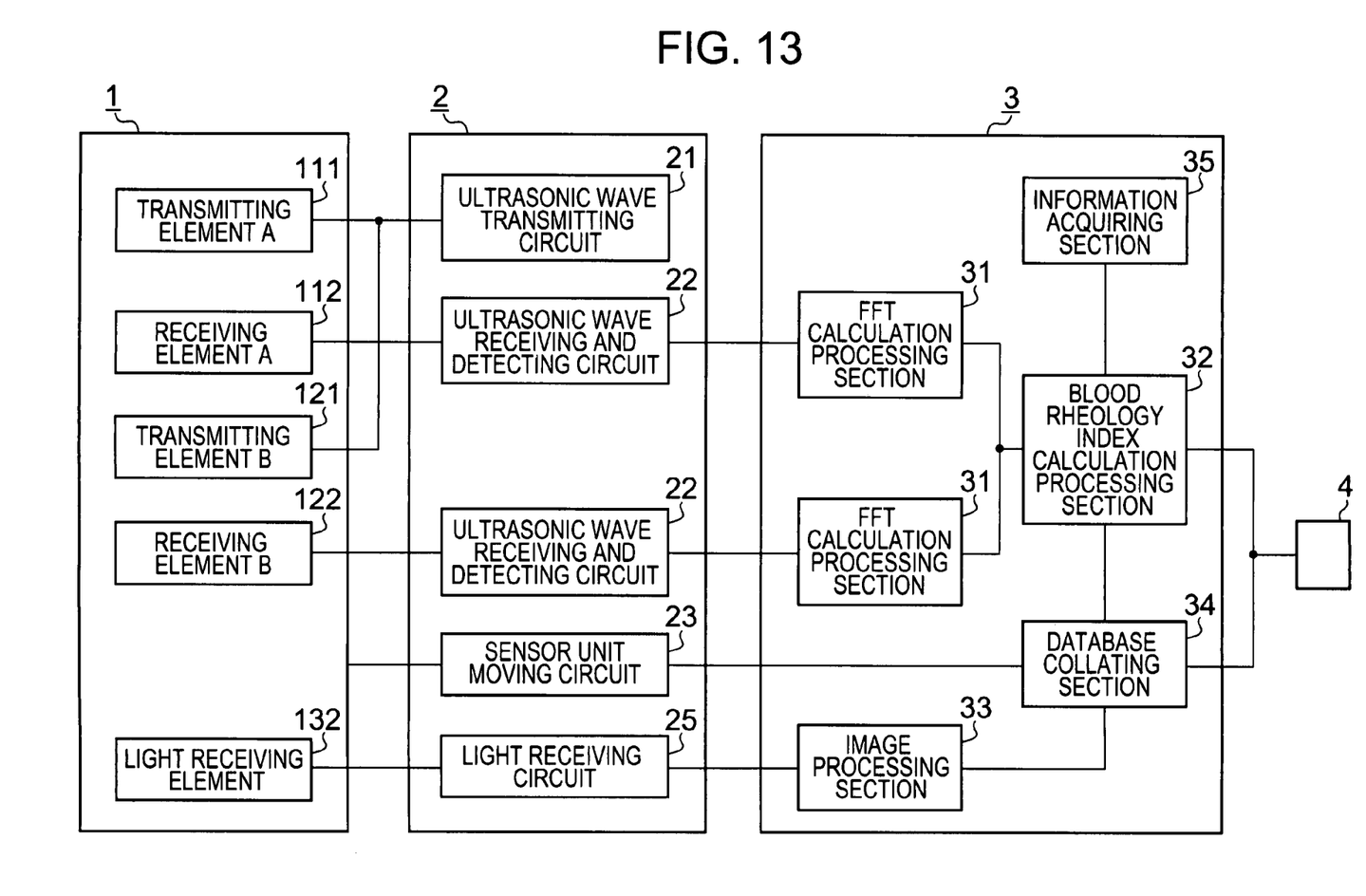
FIG. 13 is a block diagram showing one example of the constitution of the blood rheology measurement device.

FIG. 13 is a block diagram showing one example of a constitution of the blood rheology measurement device of the present invention.

Figure 14:
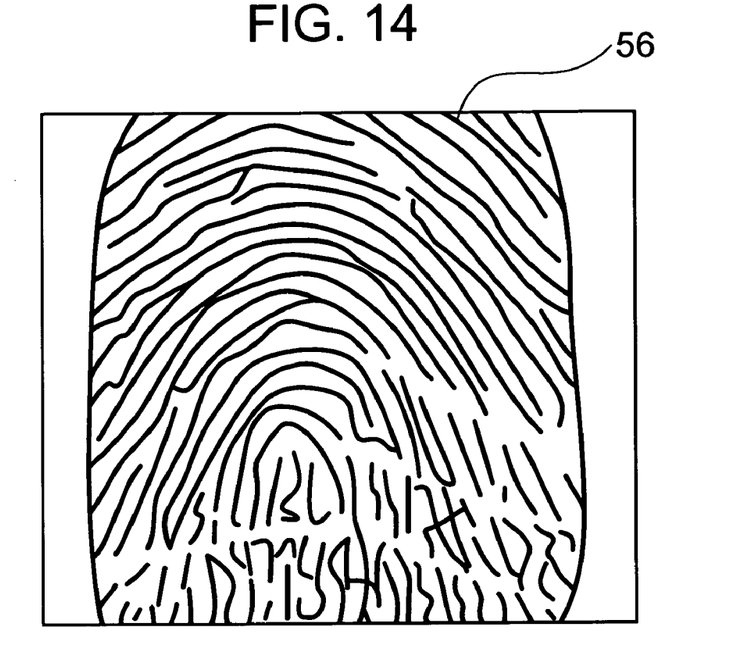
FIG. 14 is a diagram showing a fingerprint pattern.
Figure 15:
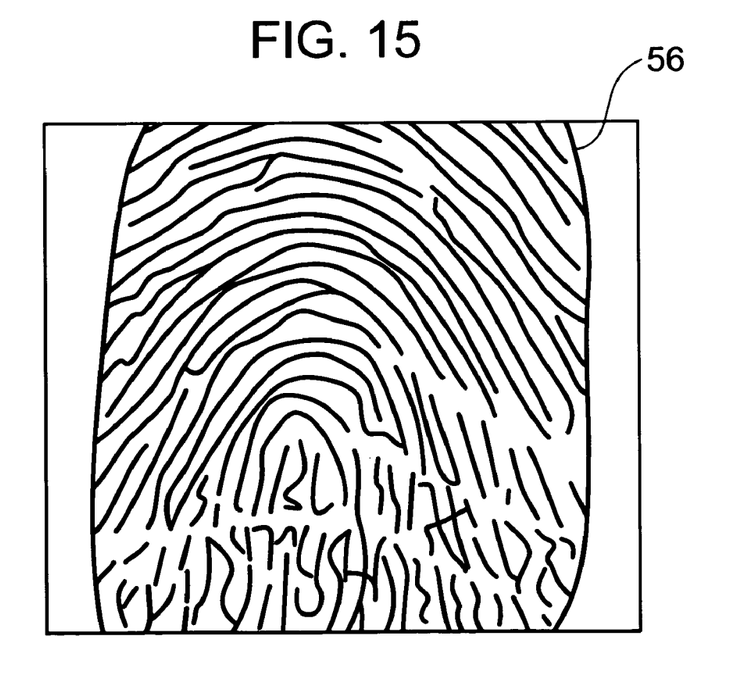
FIG. 15 is a diagram showing the fingerprint pattern.
Figure 16:
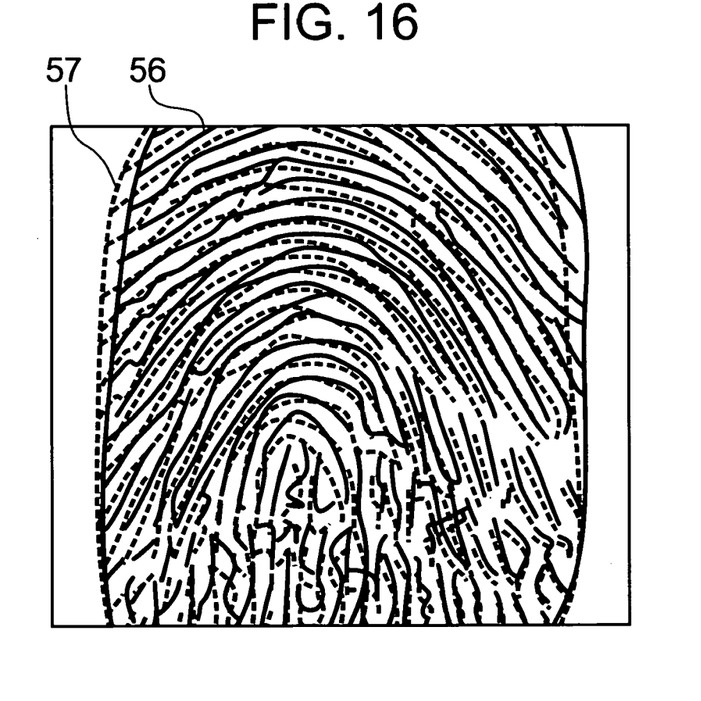
FIG. 16 is a diagram showing a comparative example of the fingerprint pattern.
Figure 17:
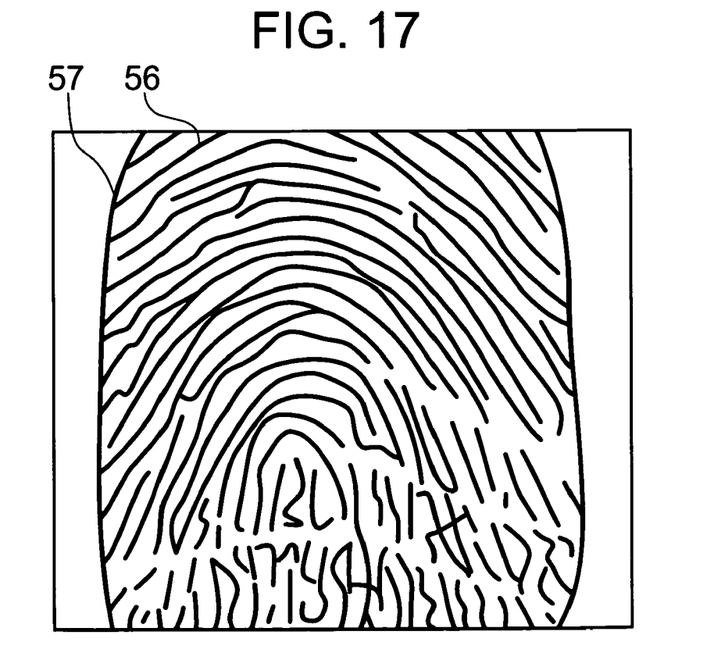
FIG. 17 is a diagram showing an example in which the fingerprint pattern is matched.

FIG. 14 shows one example of a fingerprint pattern. This is obtained by an image processing section 33 at a time when a certain subject performs measurement. This information is recorded beforehand in a database collating section 34. When this subject performs the measurement anew, a fingerprint pattern shown in FIG. 15 is similarly obtained by the image processing section 33. In this case, the fingerprint pattern recorded beforehand is read and compared (FIG. 16). When there is a discrepancy (non-registry) between a fingerprint 57 recorded in a database and a measured fingerprint 56, a sensor unit 1 is moved as shown in FIG. 17. In this state, since a positional relation between the presently measured fingerprint and the sensor unit agrees with that between the previously measured fingerprint and the sensor unit, a positional relation between the sensor unit and the artery becomes identical. Therefore, the relation between the artery 52 and the sensor unit 1 necessarily becomes consistent depending on the subject, and the measurement can be performed in a state in which the positional relation between the sensor unit 1 and the artery 52 is fixed for each subject. A method of acquiring the fingerprint is not limited to a method of obtaining the fingerprint from an image.

In the present invention, blood rheology as an index indicating a fluidity of a body fluid can be obtained without sampling blood for a medical purpose of maintaining and improving health. Since it is possible to grasp an influence of food on the blood easily and correctly, the present device may be used as an inspection device for food development.

What is claimed is:

1. A blood rheology measurement device comprising:
   detecting means having a sensor unit including an ultrasonic wave sensor section which transmits and receives an ultrasonic wave between the surface of a living body and an artery blood flow in the living body, and an image pickup section which picks up an image of the living body from the living body surface;
   image processing means having an image processing section which processes the image obtained by the image pickup section;
   an image database which stores the image processed by the image processing means; and
   blood rheology measuring means for processing a signal output from the ultrasonic wave sensor section to measure a fluidity of the artery blood flow in association with the image processed by the image processing means,
   wherein the detecting means further comprises a driving mechanism which moves a position of the sensor unit,
   the image processing means comprises
   a database collating section which collates the processed image output from the image processing section with the image stored in the image database and corresponding to the processed image; and a sensor unit moving circuit which controls the driving mechanism to move the position of the sensor unit so that the processed image and the stored image collated by the database collating section overlap with each other.

2. The blood rheology measurement device according to claim 1, wherein the processed image and the stored image are pattern images of a vein in the living body.

3. The blood rheology measurement device according to claim 2, wherein the image pickup section includes light emitting means for irradiating the living body with light and image pickup means for picking up an image of an illuminated region.

4. The blood rheology measurement device according to claim 2, wherein the database collating section has an individual authentication function of performing individual authentication by use of a vein and/or a fingerprint of the living body.

5. The blood rheology measurement device according to claim 1, wherein the processed image and the stored image are pattern images of a fingerprint of the living body.

6. A blood rheology measurement method comprising:
   an image pickup step of picking up an image of a living body from the surface of the living body;
   a blood rheology measuring step of measuring a fluidity of an artery blood flow in the living body in association with the picked-up image; and
   a storing step of storing the image obtained in the image pickup step;
   wherein the image pickup step comprises:
   an image processing step of processing the picked-up image;
   a collating step of collating the processed image and the stored image; and
   a moving step of moving a position of a sensor unit including an image pickup section which picks up the image of the living body from the surface of the living body and a detecting section which detects the fluidity of the artery blood flow in the living body so that the collated processed image and stored image overlap with each other.

7. A blood rheology measurement device comprising: a sensor unit positionable in a measurement position on a living body and having an image pickup section that picks up an image of the living body from the living body surface and a sensor section that transmits ultrasonic waves from the living body surface to an artery blood flow of the living body and receives reflected ultrasonic waves reflected from the artery blood flow; a calculation unit that calculates blood rheology of the artery blood flow based on the received reflected ultrasonic waves; an image processing section that processes the image picked up by the image pickup section to obtain a processed image indicative of the measurement position of the sensor unit relative to the living body; a database collating section that collates and superposes the processed image with an image previously stored in the database collating section and which corresponds to a previous measurement position of the sensor unit to determine whether the processed image and the stored image are in registry with one another; and a moving section that moves the sensor unit relative to the living body to position the sensor unit in a measurement position in which the processed image and the stored image are in registry with one another.

8. A blood rheology measurement device according to claim 7; wherein the processed image and the stored image are pattern images of a vein in the living body.

9. A blood rheology measurement device according to claim 7; wherein the processed image and the stored image are pattern images of a fingerprint of the living body.

10. A blood rheology measurement device according to claim 7; wherein the image pickup section includes light emitting means for irradiating the living body with light and image pickup means for picking up an image of an illuminated region.

11. A blood rheology measurement device according to claim 7; further including an output unit that displays the processed image and the stored image.

12. A blood rheology measurement device according to claim 7; wherein the database collating section has an individual authentication function of performing individual authentication by use of a vein and/or a fingerprint of the living body.

* * * * *